(12) United States Patent
Lüttgens

(10) Patent No.: US 6,976,314 B2
(45) Date of Patent: Dec. 20, 2005

(54) SHARPENER FOR SOFT-CORE PENCILS

(75) Inventor: Fritz Lüttgens, Erlangen (DE)

(73) Assignee: KUM Limited, Co. Meath (IE)

( * ) Notice: Subject to any disclaimer, the term of this patent is extended or adjusted under 35 U.S.C. 154(b) by 25 days.

(21) Appl. No.: 10/303,310

(22) Filed: Nov. 25, 2002

(65) Prior Publication Data

US 2004/0010927 A1    Jan. 22, 2004

(30) Foreign Application Priority Data

Jul. 19, 2002 (EP) ................................. 02 016 094

(51) Int. Cl.$^7$ ............................................. B43L 23/08
(52) U.S. Cl. ..................... 30/457; 30/451; 144/28.1; 422/1
(58) Field of Search ............................ 144/28.1, 28.11, 144/28; 30/451–462, 357; 422/1, 300, 301; 401/49, 96; 606/1

(56) References Cited

U.S. PATENT DOCUMENTS

| | | | | |
|---|---|---|---|---|
| 4,996,800 A | | 3/1991 | Mangus | |
| 5,167,071 A | * | 12/1992 | Eisen | 30/452 |
| 5,417,704 A | * | 5/1995 | Wonderley | 606/167 |
| 5,702,387 A | * | 12/1997 | Arts et al. | 606/45 |
| 5,845,406 A | * | 12/1998 | Luttgens | 30/454 |
| 5,983,507 A | * | 11/1999 | Hirai | 30/350 |
| 6,076,264 A | * | 6/2000 | Meckel | 30/225 |
| 6,301,791 B1 | * | 10/2001 | Luttgens | 30/454 |
| 6,330,750 B1 | * | 12/2001 | Meckel | 30/350 |
| 6,568,090 B2 | * | 5/2003 | Sheffler et al. | 30/457 |

FOREIGN PATENT DOCUMENTS

| | | |
|---|---|---|
| DE | 297 23 492 U1 | 10/1998 |
| EP | 1 043 173 A1 | 10/2000 |

* cited by examiner

*Primary Examiner*—Allan N. Shoap
*Assistant Examiner*—Phong Nguyen
(74) *Attorney, Agent, or Firm*—Henry M. Feiereisen

(57) ABSTRACT

A sharpener for sharpening soft-core pencils, especially those used in the medical or pharmaceutical field, includes a housing; and a shaping componentry, received by the housing, for shaping and sharpening a medical or pharmaceutical pencil. The shaping componentry contains a cleaning agent to thereby disinfect the pencil.

11 Claims, 3 Drawing Sheets

SHARPENER FOR SOFT-CORE PENCILS

CROSS-REFERENCES TO RELATED APPLICATIONS

This application claims the priority of European Patent Application, Serial No. EP 02 016 094.1, filed Jul. 19, 2002, pursuant to 35 U.S.C. 119(a)–(d), the disclosure of which is incorporated herein by reference.

BACKGROUND OF THE INVENTION

The present invention relates, in general, to a sharpener for soft-core pencils, and more particularly to a pencil sharpener for use with medical or pharmaceutical pencils.

A typical sharpener for soft-core pencils has a housing formed with a guide channel for receiving the pencil end to be sharpened. Accommodated in the housing is a shaping componentry comprised of a cutting blade and a core shaper. This type of sharpener is used in particular for shaping makeup or cosmetic pencils. During sharpening, the pencil is rotated within the guide channel against the cutting edge of the sharpening blade. As a consequence, the cutting edge of the sharpening blade removes a strip of outer material from the tip of the soft-core pencil and, optionally, from the core jacket. The core shaper is oftentimes integrated in the sharpener to selectively give the core tip of the pencil a relatively sharp or rounded contour.

When a sharpener is used for pencils, which are intended for direct contact with a human, it is important to take into account skin compatibility or skin care. To prevent skin irritation or even damage to the skin, pencils are used with cores of suitable chemical composition. However, subsequent reactions of the original composition, as occurring over time or as a consequence of contamination, leads to changes in the composition which have to be taken into account as well. Therefore, the hygienic demand on sharpeners of this type is high compared to typical pencil sharpeners.

It has been suggested to construct sharpeners for pencils intended for direct skin contact in a way that their functional components can be cleaned. For example, German utility model no. DE 297 23 492 U1 or European patent publication no. EP 1 043 173 A1 describe the removal of built-up soft-core mass, without damage to the cutting blade or core shaper by configuring sharpeners for cosmetic pencils with an additional dissolvable cleaning implement and a combination of the core shaper for cosmetic pencils with a cleaning device.

Still, when pencil sharpeners are involved for application in the medical or pharmaceutical field, the hygienic standards are much higher. Typically, disposable materials, such as gloves, syringes, applicators, and the like, are used for administration of drugs or for carrying out therapeutic procedures, or materials, such as suitable metal or plastics, which have to be cleaned rapidly and thoroughly. Hereby, soft-core pencils are not always useable, although their usage would be desirable in view of their easily handling.

It would therefore be desirable and advantageous to provide an improved sharpener which obviates prior art shortcomings and which allows the use of soft-core pencils also in the medical and pharmaceutical fields.

SUMMARY OF THE INVENTION

According to one aspect of the present invention, a sharpener includes a housing, and a shaping componentry, received by the housing, for shaping and sharpening a medical or pharmaceutical pencil, with the shaping componentry containing a cleaning agent for disinfecting the pencil.

The present invention resolves prior art problems by recognizing that medical or pharmaceutical pencils with chemical formulations or ingredients, which develop bactericidal, antiviral or fungicidal effect, require special care and handling as far as hygiene is concerned. Treatment especially of injured or diseased skin areas with a medical or pharmaceutical pencil may lead to contamination of the pencil or the core, when brought into direct contact with these skin areas. In order to enable a reuse of the pencil without hazard to the user, a reliable cleansing is periodically required. This is especially easy by combining the cleansing operation with other anyway required treatment techniques for the pencil. Hereby, it may be provided to subject the pencil to a cleansing process simultaneously with a possibly necessary contouring of its core. This can be ensured by appropriately configuring those components of the sharpener that come into direct contact with the medical or pharmaceutical pencil at the surface which has been treated with bactericidal, antiviral or fungicidal agents to a suitable degree. Therefore, the shaping componentry of the sharpener according to the present invention for sharpening a medical or pharmaceutical pencil is combined with a cleaning agent for disinfection of the medical or pharmaceutical pencil.

According to another feature of the present invention, the shaping componentry includes a plurality of components, each of which made of a base material, wherein the cleaning agent is added to the base material of at least one of the components as an additive, to thereby chemically disinfect the surface of the medical or pharmaceutical pencil. As a result, growth of germs on the pencil core is actively inhibited and an infection of treated areas is eliminated. Depending on the desired type and duration of the cleaning agent being used, the base material, preferably plastic material, of one or more components of the shaping componentry, may already be combined during manufacture with respective chemical additives, or the cleaning agent may also be applied later in the form of a single-layer coating or multilayer coating upon the one or more components of the shaping componentry.

The mechanical sharpening of a medical or pharmaceutical pencil removes more or less, depending on the application at hand, germs from the surface to thereby regenerate the medically or pharmaceutically active core mass. Soft-core material, which is stressed during removal and exhibits an adhesive tendency, remains attached to the sharpener. Thus, cleansing of the sharpener should be carried out in a way that an infection of other pencils, or a continuous mutual infection between a same pencil and a sharpener, or even an accumulating contamination, is avoided. In order to prevent the stressed and sticky soft-core material of the pencil to adhere to the surface of the sharpener, when the pencil is sharpened, and thus to contaminate the sharpener, the shaping componentry, and suitably also at least those parts of the sharpener that may come into contact with the soft-core material, e.g. the respective housing parts, should be provided with a surface that is configured to repel contaminants so as to be effectively clean in a passive way. This passive cleansing measure, applied in addition or as alternative to the active cleansing action, can be realized by a coating, containing polytetrafluoroethylene (PTFE), for application onto one or more of the components of the shaping componentry. PTFE is a plastic which is chemically and biologically inert as well as hydrophobic, and is commercially available under the name of Teflon. In view of its extremely low friction coefficient, Teflon is widely used as anti-stick coating. Thus, coating one or more components of the shaping componentry in this way exploits the dirt-repellent effect of this plastic material. The coating results in a quasi self-cleaning effect to reduce the contamination of the sharpener and at the same time in a decrease of a renewed strain as a consequence of the production of new medically or pharmaceutically active core mass with bacteria, viruses, fungi or the like during sharpening.

According to another feature of the present invention, the coating may have a surface displaying a structure like a lotus petal. A lotus texture provides a so-called lotus effect and refers to a microscopic nap structure which resembles a lotus petal. This structure is able to allow a trickle down of water and dirt and is designated as lotus effect. The need for a time-consuming cleaning operation is hereby eliminated. Coatings of this type are generally known to the artisan and commercially available, e.g. under the trade name "Lotus Plus" by Armstrong Holdings, Inc.

According to another feature of the present invention, the additive and/or the coating may contain a migrating substance to chemically and thus actively clean and disinfect the surface of the medical or pharmaceutical pencil. Examples of a migrating substance include bactericides, such as silver ions, which can continuously and evenly issue out of the shaping componentry. Thus, the core material of the medical or pharmaceutical pencil is constantly exposed to a cleaning agent with antimicrobial effect during the sharpening process. Suitably, the bactericidal, antiviral or fungicidal effect of the medical or pharmaceutical pencil can be optimized, when the various types of cleaning agent are combined in order to disinfect the core mass of the pencil and to keep the components of the shaping componentry clean, and applied upon one or more or all components of the shaping componentry. Components of the shaping componentry may involve the sharpening blade or the core shaper. Cleaning agent may be added to individual components or all components of the shaping componentry.

Of course, it is certainly possible to expand the application of cleaning agent to other components of the sharpener as well. For example, the housing may be made of a material containing a cleaning agent which includes an anti-stick coating and/or disinfecting chemicals, such as, e.g., silver ions.

The provision of a sharpener according to the present invention, which combines one or more components of the shaping componentry with a cleaning agent, is suitable for use in particular for medical or pharmaceutical pencils to effect a superior cleaning effect. As a result, a sharpener according to the present invention is also applicable for use with soft-core pencils, even in situations that must meet high hygienic requirements. The use of the cleaning agent as additive to the base material of one or more of the components of the shaping componentry, or as a single-layer or multi-layer coating, enables a disinfection of the pencil surface as well as cleanliness of the shaping componentry as such. The further incorporation of a migrating substance, or of polytetrafluoroethylene, or of a lotus texture, results in an especially effective use of physicochemical properties for disinfection and cleaning. Moreover, the shaping componentry as well as other components of the sharpener, e.g., the sharpener housing, may be provided with such a cleaning agent to expand the field of applications.

BRIEF DESCRIPTION OF THE DRAWING

Other features and advantages of the present invention will be more readily apparent upon reading the following description of currently preferred exemplified embodiments of the invention with reference to the accompanying drawing, in which.

DETAILED DESCRIPTION OF PREFERRED EMBODIMENTS

Figure 1:
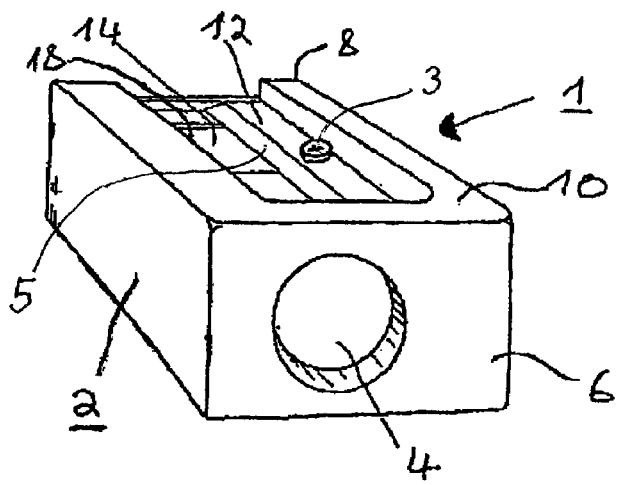
FIG. 1 is a perspective view of a sharpener according to the present invention in the direction of the pencil insertion side.

Throughout all the Figures, same or corresponding elements are generally indicated by same reference numerals.

Figure 2:
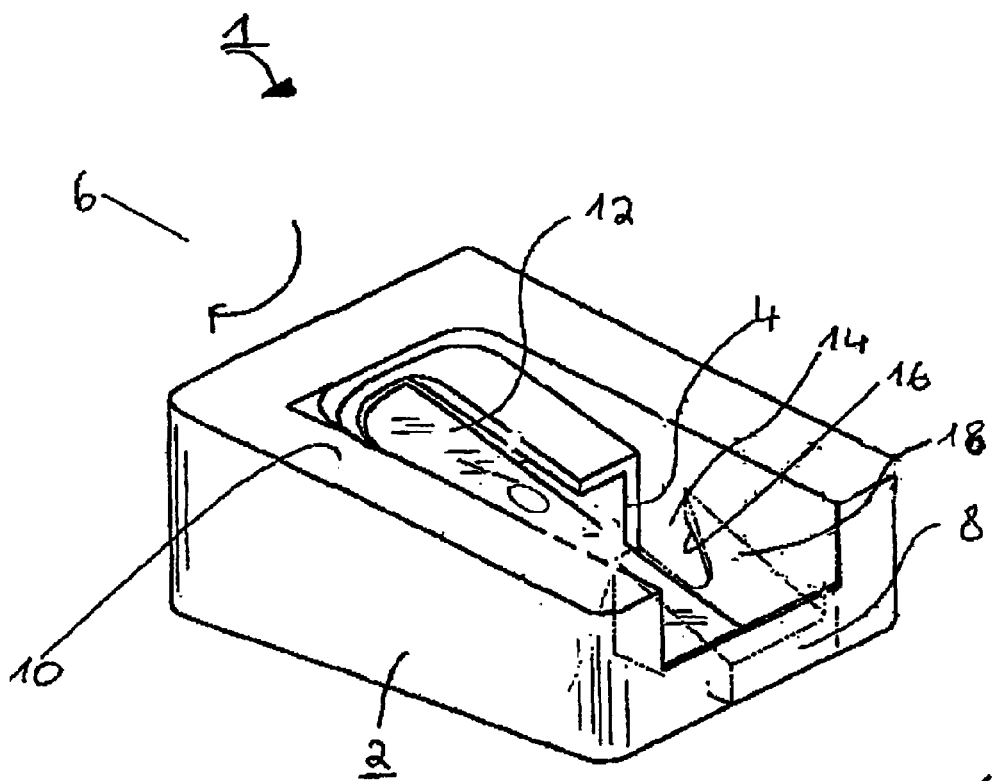
FIG. 2 is a perspective view of the sharpener in the direction of the rear side of the sharpener.
Figure 3:
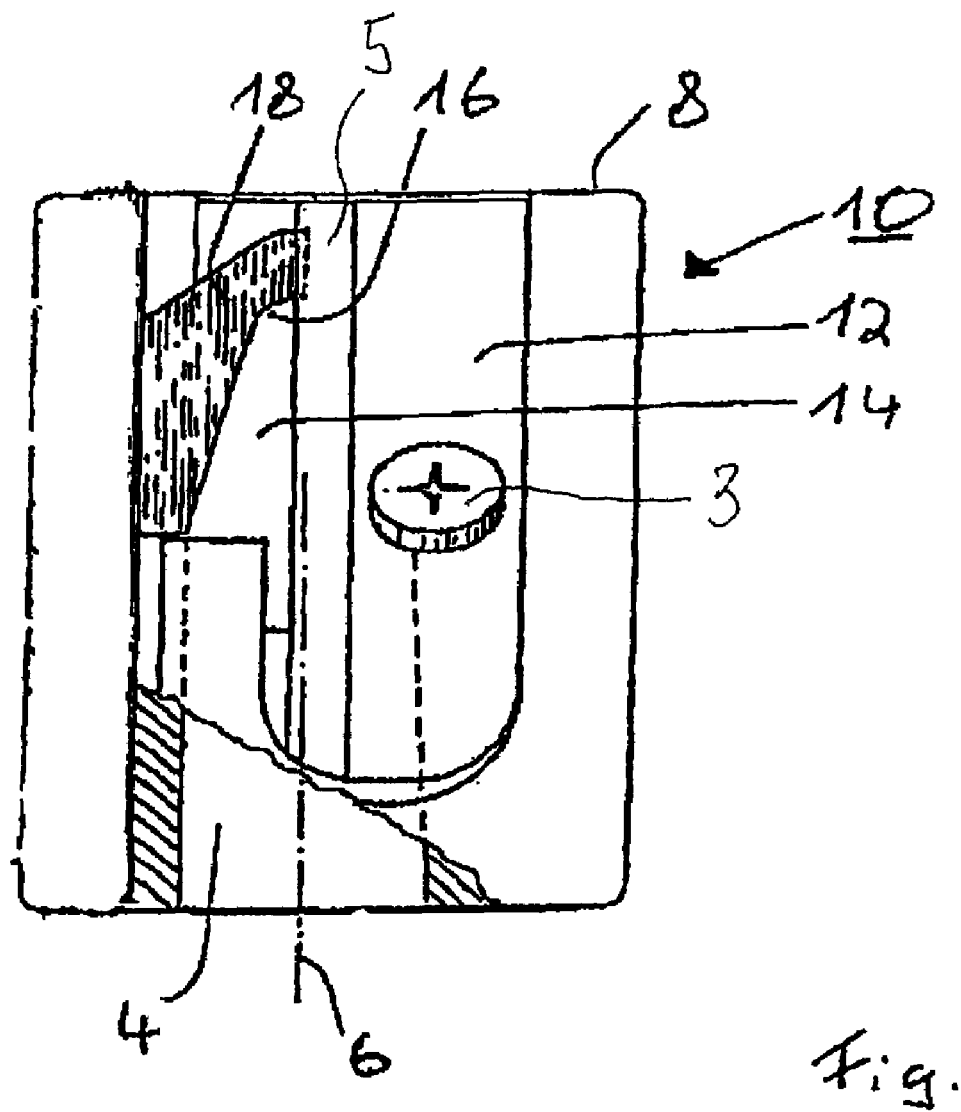
FIG. 3 is a top plan view of the sharpener.

Turning now to the drawing, and in particular to FIGS. 1 and 2, there are shown front and rear perspective views of a sharpener according to the present invention, generally designated by reference numeral 1, and including a sharpener housing 2 having a back wall 8 and a topside 10 and formed with a guide channel 4 to receive a pencil (not shown) at an insertion side 6 to sharpen the pencil into an essentially conical shape. The housing 2 supports a sharpening blade 12, which is secured by a screw 3 and extends tangentially with respect to the guide channel 4. The guide channel 4 tapers conically from the insertion side 6 of the housing 2 in the direction of a free space 14 of the housing 2, whereby the free space 14 receives the pencil cone and is positioned beneath the front end of the sharpening blade. During sharpening, the pencil is rotated against the cutting edge 5 of the sharpening blade 12 in the sharpening direction, as indicated by the arrows in FIGS. 1 and 2. As a result, the cutting edge 5 of the sharpening blade 12 removes a strip of outer material from the tip of the pencil core and, optionally, from the core jacket at the same time. In order to sharpen the core tip of the pencil with a fairly pointed contour or more rounded to avoid the risk of injury, a core shaper 18 is provided which projects into the free space 14 and is provided with a shaping edge 16, as shown in particular in FIGS. 2 and 3. The core shaper 18 may be realized in the form of an insert which is suitably removeable from the housing 2 and configured, e.g., as shaping blade or as scraping rib. The core shaper 18 is adjustable, in particular shiftable, in axial direction of the guide channel 4 within the free space 14 of the housing 2, or can be secured at varying axial distances with respect to the guide channel 4 by means of a snap connection or clamped connection.

The sharpener 1 according to the present invention is useable in particular for medical or pharmaceutical soft-core pencils and is constructed to satisfy the high hygienic demands of the medical or pharmaceutical field, which requires proper cleanliness of utilized soft-core pencils that is, of course, also affected by the sharpener as well. In accordance with the present invention, the sharpener 1 is configured for implementing a regular and reliable cleansing action of the pencil by adding a cleaning agent to those components of the sharpener 1 which effectuate the shaping process so as to realize a disinfection of the medical or pharmaceutical pencil to be sharpened. The shaping componentry includes hereby in particular the shaping blade 12 and the core shaper 18. Of course, other parts of the sharpener 1, e.g., the housing 2, may also contain a suitable cleaning agent.

There are various ways to formulate and apply the cleaning agent, as will now be described by way of example in conjunction with the core shaper 18 with reference to FIGS. 4a, 4b, 4c. It is to be understood that the principles described in the following description with respect to the core shaper 18 are generally applicable to other components of the sharpener 1 as well, such as, for example, the shaping blade 12 or the housing 2. For hygienic reasons, the core shaper 18 is made on the basis of a polymer material, but may also be made of metal or contain a metallic component. Examples of suitable polymers with antimicrobial effect include those commercially available under the trademarks SAM-Polymers® or AMINA® and distributed by Creavis GmbH, Germany. Likewise, the other components of the sharpener 1, such as the housing 2, may also be made of metal or injectable wood derivate. Of course, the other parts of the sharpener 1 may be made of same or similar materials.

To ensure clarity of the description, it is necessary to establish the definition of several important terms and expressions that will be used throughout this disclosure. As the basic composition of the components of the sharpener 1 can be suited to the application at hand, the following description uses in general the term "base material". The term "migrating substance" refers to a substance which is able to migrate constantly and evenly from the base material.

Figure 4A:
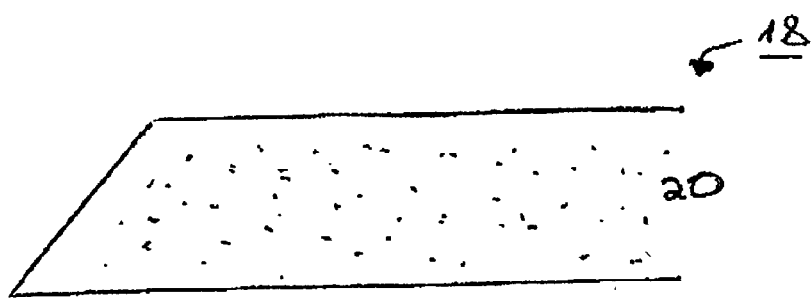
FIG. 4a is a fragmentary schematic illustration of one variation of a core shaper with cleaning agent.

Turning now to FIG. 4a, there is shown a fragmentary schematic illustration of one variation of the core shaper 18. The cleaning agent is added as additive to the base material of the core shaper 18 and includes a migrating substance 20. The incorporation of the migrating substance 20 in the cleaning agent ensures a substantially permanent wetting of the surface of the core shaper 18 with particles of the migrating substance 20. Thus, the migrating substance 20 may be used to disinfect the pencil and its core, when periodically contacting the sharpener 1 during sharpening process. Examples of migrating substance 20 include disinfecting or antimicrobial substances, e.g. silver ions. This type of substance migrates out of the base material and contacts the surface of the medical or pharmaceutical pencil and its core, when sharpened, to develop there its bactericidal effect.

As a medical or pharmaceutical pencil is mechanically sharpened, the surface contaminated by bacteria, viruses, fungi or other germs is removed to thereby regenerate the medically or pharmaceutically active core mass. To prevent renewed contact of this fresh core material with removed contaminated soft-core material via the core shaper 18, the surface of the core shaper 18 is made repellent to contaminants through application of a coating 22 (FIG. 4b) or coating 24 (FIG. 4c) to thereby realize a quasi self-cleaning action. An example of a suitable coating involves a coating on the basis of polyammonium salts.

Figure 4B:
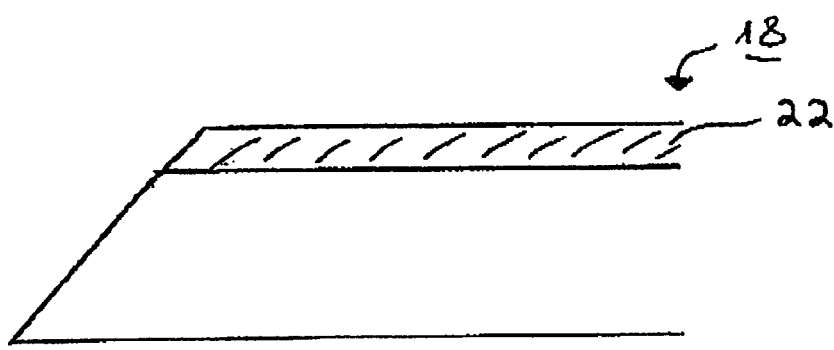
FIG. 4b is a fragmentary schematic illustration of another variation of a core shaper with cleaning agent.

In FIG. 4b, the coating 22 is made of polytetrafluoroethylene to exploit its anti-stick properties so that neither water nor dirt is able to even partially penetrate. As a result of this physicochemical effect, adherence to the core shaper 18 of soft-core material, despite its sticky property, is prevented.

Figure 4C:
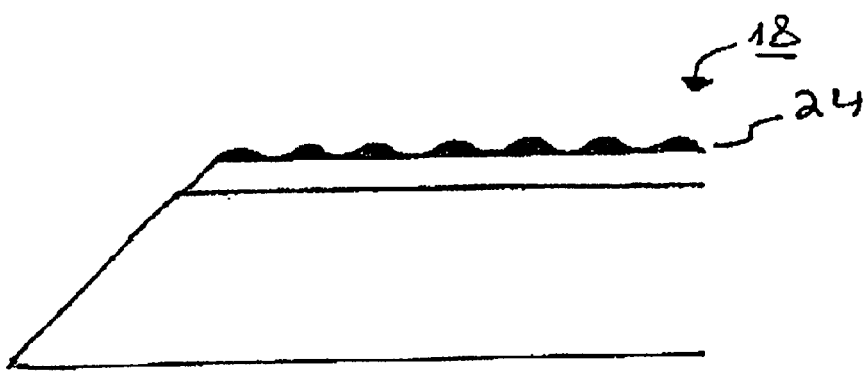
FIG. 4c is a fragmentary schematic illustration of yet another variation of a core shaper with cleaning agent.

In FIG. 4c, the coating 24 is so configured as to exhibit in the area of the surface a lotus texture, as indicated by the wavy illustration. This microscopic nap structure results in a physical trickle down of dirt and water. This effect is called "lotus effect". Thus, contamination of the core shaper 18 is avoided and the risk of a renewed contamination of a fresh medically or pharmaceutically active mass, as emerging after a sharpening operation, by bacteria or other germs, is significantly decreased.

There are innumerable ways of formulating a suitable cleaning agent for use here, only several of which will be detailed here. However, other compositions of the cleaning agent which generally follow the concepts outlined here are considered to be covered by this disclosure. Likewise, any number of components or parts of the sharpener 1 may be treated with a cleaning agent, without departing from the spirit of the present invention. Thus, cleaning agent may be applied to some or all parts of the sharpener 1, including shaping componentry and sharpener housing 2, to accomplish a disinfection of the core mass of the pencil and maintain cleanliness of the sharpener 1, SO that the medical and pharmaceutical pencil may reliably develop, e.g., its bactericidal, anti-viral or fungicidal effect.

While the invention has been illustrated and described in connection with currently preferred embodiments shown and described in detail it is not intended to be limited to the details shown since various modifications and structural changes may be made without departing in any way from the spirit of the present invention. The embodiments were chosen and described in order to best explain the principles of the invention and practical application to thereby enable a person skilled in the art to best utilize the invention and various embodiments with various modifications as are suited to the particular use contemplated.

What is claimed is:

1. A sharpener, comprising:
   a housing having a guide channel to receive a medical or pharmaceutical pencil, said guide channel tapering conically from an insertion side of the housing to a free space to receive a core end of the pencil; and
   a shaping componentry, received by the housing, for shaping and sharpening a medical or pharmaceutical pencil, said shaping componentry including a blade supported by the housing and extending tangentially in relation to the guide channel for sharpening the care end, and a core shaper projecting into the free space for shaping the core end of the pencil,
   wherein the shaping componentry contains a cleaning agent for disinfecting the core end of the pencil.

2. The sharpener of claim 1, wherein the blade and the core shaper of the shaping componentry are each made of a base material, wherein the cleaning agent is added to the base material of at least one of the blade and core shaper as an additive.

3. The sharpener of claim 1, wherein the blade and the core shaper of the shaping componentry are each made of a base material, wherein the cleaning agent is applied on the base material of at least one of the blade and core shaper in the form of a coating selected from the group consisting of a single-layer coating and multi-layer coating.

4. The sharpener of claim 3, wherein the coating contains polytetrafluoroethylene.

5. The sharpener of claim 3, wherein the coating has a surface displaying a lotus texture.

6. The sharpener of claim 2, wherein the additive contains a migrating substance.

7. The sharpener of claim 3, wherein the coating contains a migrating substance.

8. The sharpener of claim 6, wherein the migrating substance includes silver ions.

9. The sharpener of claim 7, wherein the migrating substance includes sliver ions.

10. The sharpener of claim 1, wherein the housing is made of a material containing said cleaning agent.

11. The sharpener of claim 1, wherein the housing includes a housing part having a surface which is treated with a contamination-repellent agent.

* * * * *

UNITED STATES PATENT AND TRADEMARK OFFICE
CERTIFICATE OF CORRECTION

PATENT NO. : 6,976,314 B2
APPLICATION NO. : 10/303310
DATED : December 20, 2005
INVENTOR(S) : Fritz Lüttgens Page 1 of 1

It is certified that error appears in the above-identified patent and that said Letters Patent is hereby corrected as shown below:

On the title page item
[73] Assignee: after "KUM Limited," insert --IE-Trim--;

Column 6 line 9: change "SO" to --so--;

Column 6 line 33: change "care" to --core--.

Signed and Sealed this

Fifteenth Day of August, 2006

JON W. DUDAS
*Director of the United States Patent and Trademark Office*